United States Patent [19]

Simon et al.

[11] 4,425,810

[45] Jan. 17, 1984

[54] APPARATUS FOR PHYSICAL PROPERTIES MEASUREMENTS AT HIGH TEMPERATURES AND PRESSURES

[75] Inventors: Ralph Simon, Placentia; Raymond L. Schmidt, Whittier, both of Calif.

[73] Assignee: Chevron Research Company, San Francisco, Calif.

[21] Appl. No.: 318,506

[22] Filed: Nov. 5, 1981

[51] Int. Cl.³ ............................................. G01N 1/28
[52] U.S. Cl. .......................... 73/863.11; 73/864.91; 374/45
[58] Field of Search ............... 73/151, 863.11, 864.81, 73/864.91; 374/45

[56] References Cited

U.S. PATENT DOCUMENTS

| | | | |
|---|---|---|---|
| 4,042,333 | 8/1977 | Dell et al. | 73/23 X |
| 4,175,424 | 11/1979 | Bimond et al. | 73/864.91 |
| 4,296,637 | 10/1981 | Calamur et al. | 73/863.11 |

Primary Examiner—James J. Gill
Attorney, Agent, or Firm—G. W. Wasson; Edward J. Keeling; Lewis S. Gruber

[57] ABSTRACT

An apparatus is disclosed for measuring physical properties of a sample material at controllable temperatures and pressures. The apparatus includes a sample cell for holding fluid and/or solid samples. The cell includes at least one optically transparent window permitting visual and electromagnetic energy observations of the sample. A probe functions within the cell to collect a subsample for movement to apparatus for measuring properties and for returning the subsample to the cell. One form of optically transparent window is a sapphire. The cell is intended for measurements of physical properties at temperatures from about −40° F. to about +400° F. and at pressures from vacuum to at least 20,000 pounds per square inch.

24 Claims, 5 Drawing Figures

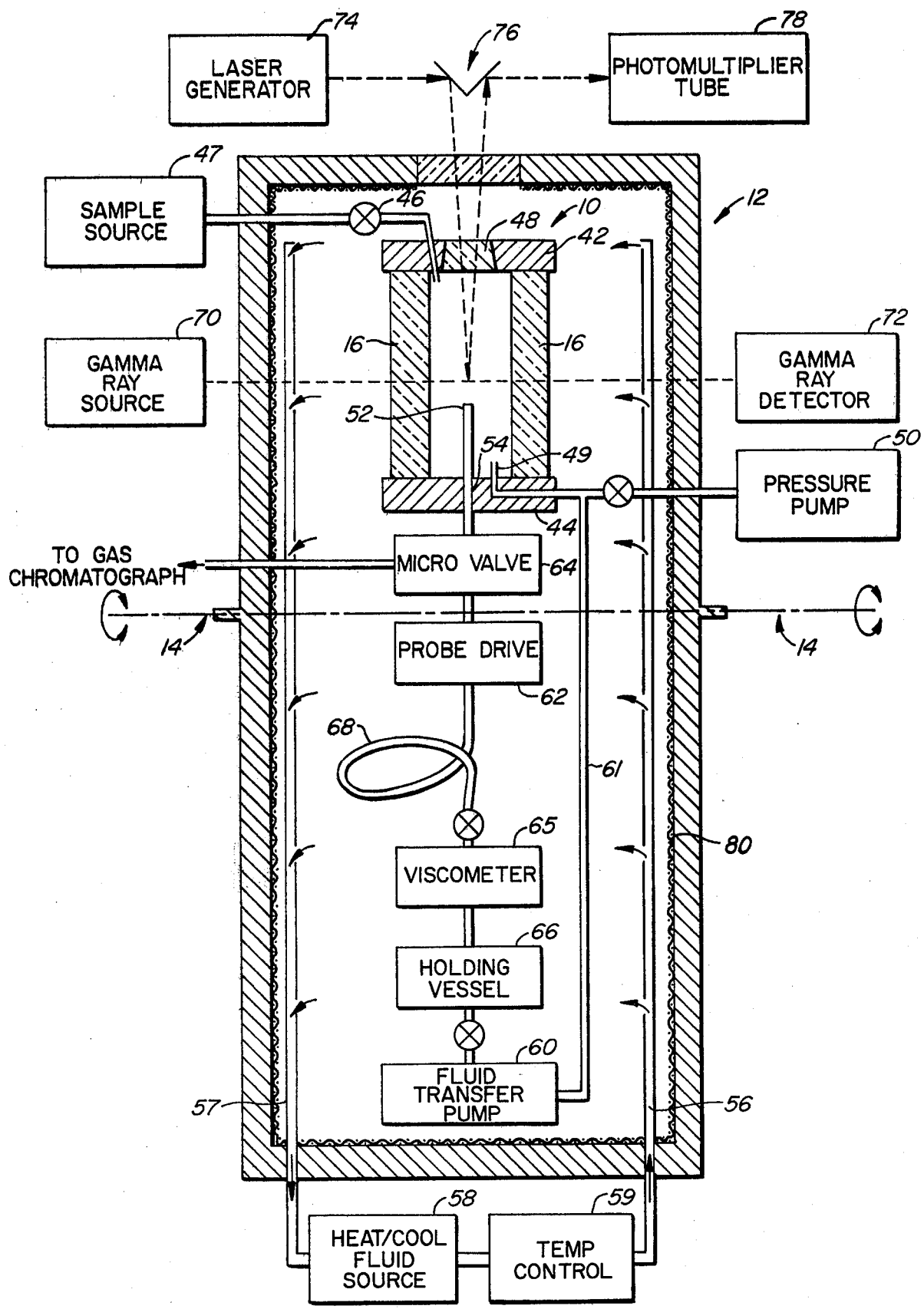
FIG._1.

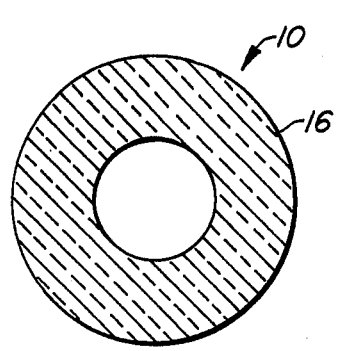
FIG._2.
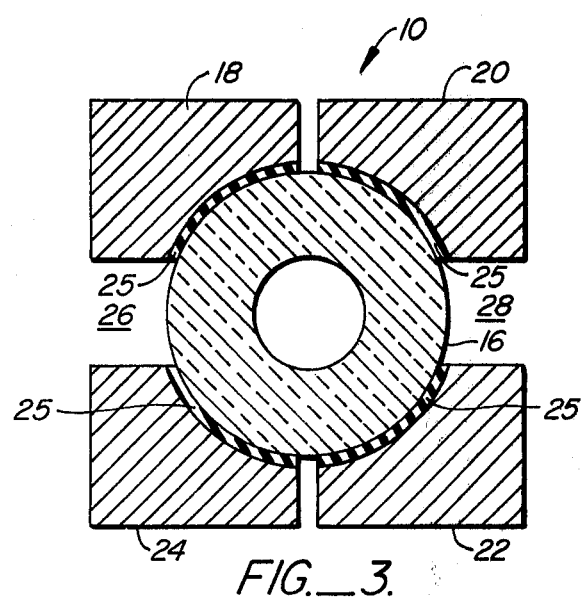
FIG._3.
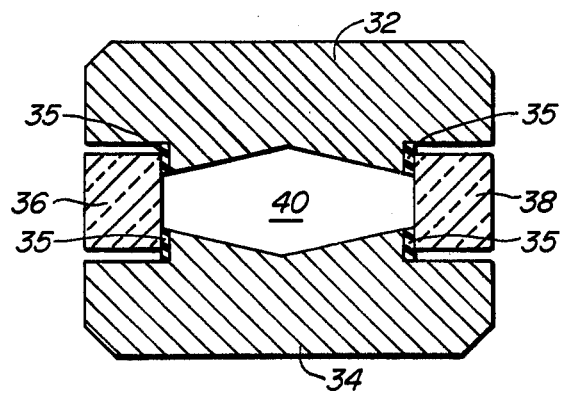
FIG._4.
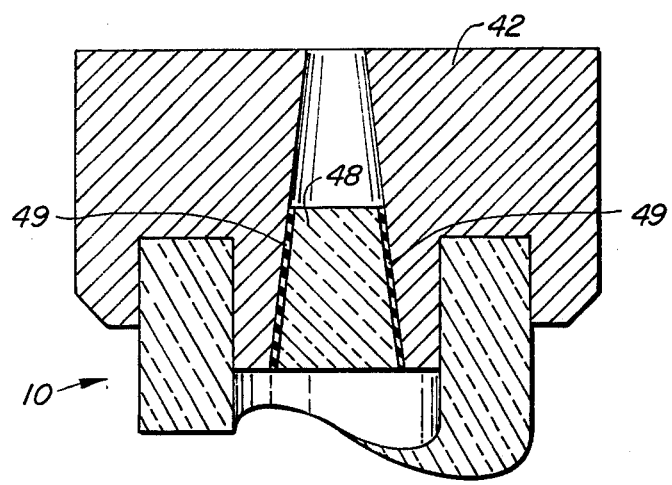
FIG._5.

APPARATUS FOR PHYSICAL PROPERTIES MEASUREMENTS AT HIGH TEMPERATURES AND PRESSURES

This invention relates to an apparatus useful in measuring the physical properties of a sample material at controllable temperatures and pressures. More particularly the apparatus is useful in measuring physical properties of a sample maintained at high temperature and high pressure.

BACKGROUND OF THE INVENTION

Field of the Invention

The physical properties of materials, i.e., composition, density, viscosity and interfacial tension (liquid/liquid or liquid/gas) are dependent upon the temperature and pressure applied to the samples when those measurements are made. Not only does the state i.e., gas, liquid or solid, of the sample depend upon the temperature and pressure applied to the sample but also, where two materials are involved, as in a mixture, the relationship between the two materials may be sensitive to the temperature and pressure.

Knowing that a physical property of a material varies with temperature and pressure, may not always permit the calculation of that physical property from measurements at ambient temperature and pressure to a different temperature and pressure. There are many possible unknown variations which may affect a physical property of a material as it is subjected to different temperatures and pressures. In that regard, there is no real substitute for accurate measurement of a physical property at the temperature and pressure in question. For example, the measurement of physical properties of a sample taken from a subsurface earth formation where the pressure may be 20,000 pounds per square inch (140 MPa) or higher and the temperature may be 400° F. (205° C.) or higher. If physical properties of such a sample were measured at the ambient temperature and pressure at the earth's surface, the measured properties would not likely be meaningful for physical properties at the subsurface temperature and pressure.

It has been known that, in the case of measuring physical properties of subsurface earth formation samples, physical properties of samples should be measured at the subsurface temperature and pressure. Prior art methods of which we are aware separate a sample into smaller portions and subject the individual portions to the desired temperature and pressure then measure a specific physical property such as density or viscosity. The sample is frequently destroyed in the measurement and thereafter no longer available. Such methods have been costly and time consuming frequently taking several weeks of time even in well-equipped measuring and testing facilities. We are further unaware of apparatus that can be used in such prior art measurements that will permit actual visible observation of the sample during measurement of physical properties at the elevated temperatures and pressures.

SUMMARY OF THE INVENTION

In accordance with our invention, a sample of material whose physical properties are to be measured, is placed in a sample cell and there subjected to the temperature and pressure applied to the sample when the unknown physical properties are desired to be measured. The sample cell includes a probe for selecting portions of the sample within the cell for transportation, if necessary, to a measuring device. The sample is also observable through a transparent window so that observations and measurements may be made on physically observable portions of the sample. The entire sample cell, and supporting apparatus is designed to withstand high temperatures and pressures and is further designed to provide safety protection to a user of the apparatus. Samples placed in the cell are subjected to non-destructive measurements of most physical properties, with the exception of compositional measurements by gas chromatography, and the samples transported to separate measuring devices are returned to the sample cell to be available for measurement of other physical properties. The sample is pressurized with a non-contaminating fluid and the separated portion of the sample is transported to measurement apparatus with the aid of the non-contaminating immiscible fluid.

Further, the apparatus provides transparent windows for both observation of the sample and for transmission of electromagnetic energy that can be used in measuring certain physical properties of the sample.

The sample cell is rotatable about an axis that permits observation of the sample through the transparent windows when the sample is under the influence of gravity forces, as well as mixing and equilibration of the various liquid and vapor phases within the cell.

The entire apparatus of the present invention is intended to be self contained and designed to permit the measurement of physical properties of a sample under controllable temperatures and pressures in a safe and expeditious manner.

The objects and features of the present invention will be readily apparent to those skilled in the art from the appended drawings and specification illustrating a preferred embodiment wherein:

FIG. 1 is a schematic representation of the combined measuring apparatus of the present invention.

FIG. 2 is a sectional view through one form of the sample cell of the present invention illustrating a single cylindrical configuration.

FIG. 3 is a sectional view through an alternative form of a sample cell and holder.

FIG. 4 is a further alternative form of a sample cell with transparent windows.

FIG. 5 is a sectional view through an end cap of the sample cell illustrating construction providing a transparent window in the end cap.

DESCRIPTION OF PREFERRED EMBODIMENTS

The apparatus of the present invention as illustrated in FIG. 1 in a schematic form incorporates the features of a sample cell 10 adapted to withstand a specification for high temperatures and high pressures while providing visual and physical access to the sample material contained within the cell. Surrounding the sample cell are the various apparati which would be used for measuring physical properties of materials within the sample cell and all of the apparatus is supported within a housing 12 adapted to be pivotted about an axis 14.

The sample cell of the present invention is preferrably constructed in the form shown in FIG. 2 having a hollow cylindrical cross-section and a construction of an optically transparent material. It has been determined that the material for the sample cell may be constructed from sapphire 16 with a polished exterior surface and a polished interior surface to provide for the desired optical and strength characteristics. Further details of the sapphire construction will be described hereinafter.

An alternative for the sapphire cell construction is shown in FIG. 3 with the sapphire hollow cylinder 16 supported within structural exterior members 18, 20, 22 and 24 with gasket material 25 between the cylinder 16 and the structural members. The structural members 18 and 24 and the members 20 and 22 are separated to provide a visual path at 26 and 28, respectively, for visual observation through the sample cell.

A further alternative sample cell construction is illustrated in FIG. 4 where structural members 32 and 34 support a pair of optically transparent members 36 and 38 to provide visual pathways into the interior area 40 where samples may be contained. Gasket material 35 separates the structural members and the transparent members.

Referring again to FIG. 1, the sample cell of any of the constructions (FIGS. 2, 3 and 4) is supported within the interior of the housing 12 and is provided with a top head at 42 and a bottom head at 44. The two heads are secured together by structural members, not shown, to provide a complete seal of the interior of the sample cell in a matter to withstand the temperatures and pressures that are desired for the test procedures to be conducted on the samples within the container. While structural members that secure the top head, bottom head and the sapphire material 16 in the place are not shown, it should be understood that the construction and the engineering mechanics that provide for the complete sealing of the container are essential to the proper operation of the apparatus; however, they are details which do not form a limitation on the present invention.

The top head 42 is provided with a valving system 46 that permits samples to be introduced into the cell without contamination. The samples may be supplied from a sample source 47 which may include the samples at ambient temperatures and pressures. The top head is further provided with a window 48 supported in gasket material 49, as shown in FIG. 5, which permits optical access into and out of the cell to permit measurements from surfaces of the samples in the container. The bottom head 44 is provided with an entry system for pressurizing the interior of the sample cell. The system herein shown includes a pressure conduit 49 passing through the head 44 into the interior of the sample cell 10 from pressure pump 50. The lower head 44 also provides a passage way for access to a probe 52 with the passage way 54 providing both means for moving the probe within the cell and for controlling the capturing of samples of the materials within the cell.

The interior of the housing 12 is provided with a system for controlling the temperature within the cell; the system herein illustrated includes an inlet conduit 56 supplied with heated or cooled fluid and an exit conduit 57 for circulating the fluid from heat/cool fluid source 58. A temperature control apparatus 59 permits the fluid to be heated or cooled, as desired, to provide both heating and cooling for the sample cell.

The pump 50 functions to supply the pressure to the interior of the sample cell, while fluid transfer pump 60 provides a balancing force pressure through conduit 61 to lower head 44 for maintaining the sample cell at a constant pressure while smaller portions of the sample are withdrawn from the cell through the probe 52.

The probe 52 is positioned within the interior of the sample cell by operation of probe drive 62 which moves the probe inside the cell through the passage way 54. Samples taken from within the cell at the probe may be transported through the probe drive conduit to a micro sample holder 64 where the sample may be transported to other test facilities at the temperature and pressure contained within the sample cell and returned to the sample cell, if necessary, to maintain the sample in integrity. A holding vessel 66 is designed to withstand the pressure and temperature of the sample cell and is connected through a viscometer 65 and a flexible loop 68 to the sample holder 64 and to the probe 52 through probe drive 62 to permit samples to be taken from the interior of the sample cell at the pressure within the cell in a manner to be more fully described hereinafter.

The apparatus thus far described provides a sample cell which may be controlled in temperature and pressure, which may contain samples that may be observed through visual observation windows, and which may be heated or cooled and pressurized to any desired temperatures and pressures. A sample probe operates within the cell and permits portions of the sample within the cell to be withdrawn for testing in suitable test facilities.

In accordance with the features of the present invention physical properties of the sample within the cell may be measured at the temperature and pressure within the cell by transporting a portion of the sample to measurement facilities or by bringing measurement apparatus into alignment with the sample cell. One form of such apparatus is illustrated by a gamma ray source 70 which may be aligned with the optically transparent windows 16 of the cell to permit gamma rays to be passed through the sample within the cell to a gamma ray detector 72. The density of any phase in the sample cell may be measured by gamma ray transmission wherein the intensity of the gamma rays transmitted through the cell is a function of the electron density (therefore the actual density) of the material in the cell. Procedures for determining the density by this method have been described in Review of Scientific Instruments, Volume 44, 313 (1973) in an article by F. E. Levert, I. G. Villon, and H. J. Tarng titled "High Temperature Density Apparatus Using The Photon Attenuation Technique".

Between the holding vessel 66 and sample cell 16 there is provided a viscometer 65 housing a torsional crystal. In the viscometer the torsional crystal is surrounded by a portion of the sample withdrawn by the probe in the sample cell so that the torsional crystal will be surrounded by the sample material at the temperature and pressure within the sample cell. The viscosity of the material within the cell may then be determined by the effect of the sample on the torsional crystal. The piezoelectric quartz crystal is in a tuned, resonant electronic circuit. The viscosity of the material surrounding the piezoelectric quartz crystal provides an additional damping force on the crystal oscillation which changes the characteristics of the resonance circuit. The changing characteristics may then be related to the viscosity of the material surrounding the crystal. This technique has been described by the National Bureau of Standards in an article in Physica, Vol. 67, 440 (1973) by W. M. Haynes titled "Viscosity of Gaseous and Liquid Argon", and California Institute of Technology in the Journal of Chemical Physics, Vol. 60, 3109 (1974) in an article by H. J. Strumpf, A. F. Collings and C. J. Pings "Viscosity of Xenon and Ethane in the Critical Region".

In the measurement of viscosity by the techniques just described, the samples withdrawn from the sample cell are returned to the cell for further analysis.

Compositions of the phases of the materials within the sample may be determined by withdrawing samples through the probe to the micro valve 64 where a portion of the sample may then be transported, by suitable conveying gases such as helium or special solvents, to a gas chromatograph which may be incorporated into the apparatus of the present invention or may be a separated conventional chromatograph system. The sampling probe 52 is movable within the sample cell so as to permit the withdrawal of a sample of any phase of the materials within the sample cell. Further, the probe is designed to permit the probe to be flushed by the material within the sample cell to minimize contamination from previous samples which may have been contained within the sample cell. A small sample of the material contained within the cell may be passed through a gas chromatograph to provide complete compositional information concerning the material in the cell. For example, a sample may range in volume from 1 microliter to 300 microliters, although the present invention is not limited to this range.

The optically transparent material 16 used in the construction of the sample cell permits visual observations to be made on the materials within the cell. In that regard, visual observations may be used to determine the interfacial tension between phases of the materials within the cell. With benefit of the optically transparent window one such technique is the pendant drop method as described in an article in Review of Scientific Instruments, Vol. 39, 386 (1968) by V. Schoettle and H. Y. Jennings titled "High Pressured, High Temperature, Visual Cell for Interfacial Tension Measurements". Further, with the ability to rotate the sample cell about axis 14, it is possible to make measurements between gas and oil by displacing a drop of oil from the tip of the probe within the sample cell, photographing the drop, and measuring its volume. The measured volume plus the gas and oil densities which have been previously measured or calculated can then be used to calculate interfacial tension. Gas-water and oil-water interfacial tensions can be determined in a similar manner without inverting the cell by passing drops of the one material through the other material using the fluid transfer pump 60 and observing its behavior in the other phase. It is also possible to count the bubbles of the less dense fluids rising through the more dense fluids at a constant flow rate to determine interfacial tension. A technique for measuring interfacial tension in that manner is shown and described in U.S. Pat. No. 4,196,615 issued Apr. 8, 1980 to Bruce W. Davis for "Method and Apparatus for Field Measurement of Interfacial Tension Between Immiscible Fluids" and in Review of Scientific Instruments, Vol. 52, pp. 590–593 (1981) by T. Ohsawa and T. Ozaki in an article titled "New Method For Determination Of Surface Tension Of Liquids".

An additional and independent method for measuring viscosity and interfacial tension is also possible with the apparatus of the present invention through the use of techniques known as photon correlation spectroscopy as described in an article in Photon Correlation Spectroscopy and Velocimetry by H. Z. Cummins and E. R. Pike from Plenum Press, New York (1976) in an article titled "Light Scattering by Liquid Surfaces" with authors D. Langevin and J. Meunier and in an article in Journal de Physics, Vol. 35, 857 (1974) by J. C. Herpin and J. Meunier titled "Spectral Study Of Light Scattering From The Thermal Functions Of The Liquid Vapor Interface Of $CO_2$ Near Its Critical Point. Surface Tensions And Viscosity Measurements".

To accomplish the photon correlation spectroscopy method a laser generator 74 is focused and its beam is reflected by mirrors 76 and transmitted into the sample cell through the sapphire window 48 in the top head 42. The laser beams that are scattered and reflected from the vapor-liquid or liquid-liquid interface, leave the cell through the same window and then are directed by mirrors 76 to a photon correlation spectroscopy detecting system employing a photomultiplier tube 78. The photon correlation spectroscopy system measures the intensity fluctuations of the light scattered by the movement of the vapor-liquid or liquid-liquid interface, and provides the power vs. frequency spectrum used to calculate viscosity and interfacial tension. For that purpose it is necessary to know the densities of both phases of the material within the sample cell as may be measured by the apparatus previously described.

The fluid pressure within the sample cell is controlled by pressure pump 50 by changing the fluid volume with a piston operating within the pressure pump 50. One pressure transfer material useful in this apparatus is mercury. By using mercury the materials within the cell are not contaminated by the pressurizing system and the mercury itself continues to be a liquid phase throughout the ranges of temperatures and pressures for which the cell is designed. Transfer of samples from the cell to the various measurement equipment is effected by fluid transfer pump 60 which moves the samples into and out of the probe with mercury at the pressure within the cell.

Fluid temperatures are controlled within the sample cell and measurement equipment by circulating a fluid medium, from source 58, within housing 12. A preferred fluid medium is nitrogen. The nitrogen is either heated or cooled to the desired temperature, by temperature control 59, and circulated within the housing through conduits 56 and 57. For example, a sample cell may be cabable of maintaining a range of temperatures between about −40° F. and about +400° F., although the present invention is not limited to this range.

The apparatus of the present invention is provided with additional safety features which protect both the equipment and its operators in the event of failure of the system. Because the system is designed to be operated at elevated temperatures and pressures and because the apparatus has an objective of being used in the measurement of physical properties of combustible hydrocarbon materials, it is desirable to design the system to prevent it from becoming an explosive apparatus. To accomplish that purpose the exterior housing 12 is constructed of high tensile strength materials, such as steel, and the interior of the housing is provided with a lining 80 of flexible fabric, one form of which is sold under the trade name Kevlar by the DuPont Corporation. Kevlar provides a substantially explosion proof enclosure for the apparatus to prevent particles of the apparatus from flying through the exterior housing.

To further prevent explosion within the system the temperature control system is provided by the nitrogen atmosphere to prevent a combustible or explosive mixture from forming within the testing apparatus. Further, the nitrogen atmosphere surrounding the entire sample cell is kept at a slight vacuum with respect to outside pressures to prevent releasing vapors from within the apparatus to the area surrounding the apparatus.

It has been found with the apparatus of present invention the physical properties such as composition, density, viscosity and interfacial tensions of the vapor and liquid phases that may be measured and determined in a substantially reduced time with respect to other known forms of apparatus for measuring these same properties. In addition, because the sample cell provides an optically transparent system for observing events that occur within the sample cell, it is possible to measure relative phase volumes, to find bubble and dew points, and to examine multiple liquid phases, detecting solids that form as temperatures and pressures are changed and to observe the formation of emulsions that complicate measurements of other physical properties of the sample materials. While the apparatus has particular application to the measurement of physical properties of petroleum based materials from an earth formation, it is also possible to measure physical properties of other non-hydrocarbon base materials and particularly to measure the effect of and interaction between hydrocarbon materials and non-hydrocarbon materials which may be used in high pressure reservoirs or high pressure systems.

In the construction of the sample cell it has been determined that the preferred material for providing the transparent optical system is a sapphire tube manufactured from a single crystal of 0° orientation. Alternative crystalline forms for construction of the sample cell include high strength glass, diamond and salt crystals (for example transparent crystalline salts of alkali metals, such as sodium and cesium or the alkaline earth metals such as calcium, and other window materials used in laser devices). The tube is constructed from the single crystal, then cored by drilling and polished by mechanical and chemical methods. The tube is then glazed to eliminate surface imperfections, to add strength and to minimize the adverse effects of moisture and corrosive gases. An alternative form of sample cell provides a pair of sapphire windows which are supported within a steel housing. In this case the sapphire windows are also manufactured of a single crystal of 0° orientation with the surfaces polished by the mechanical and chemical methods to avoid the imperfections of the surfaces. While the sapphire windows of FIG. 4 provide windows that are more easily fabricated than the sapphire tube of FIGS. 2 and 3, the overall system itself is not as easily manufactured in that the windows must be securely sealed within the sample cell to maintain the high temperatures and high pressures that are anticipated.

The configuration shown in FIG. 3 provides for additional strength and reduces the tensile stresses on the cell due to the temperature and pressures within the cell.

The upper head form shown in FIG. 5 provides a head 42 with the window 48 allowing visual passages into and out of the cell 10. The design features of the seal between the head and the visual cell do not form a critical part of the present invention, it being understood that the design must be able to withstand the intended pressures and temperatures at which the apparatus is intended to be used.

While certain preferred embodiments of the invention have been specifically disclosed, it should be understood that the invention is not limited thereto as many variations will be readily apparent to those skilled in the art, and the invention is to be given its broadest possible interpretation within the terms of the following claims.

We claim:

1. Apparatus for measuring physical and chemical properties of fluid and/or solid systems including composition, density, viscosity and interfacial tension of a sample, said measurements being conducted at controllable temperature and pressure, said apparatus comprising:
    (a) a sample cell and means for inserting a sample into said sample cell, said sample cell being capable of maintaining said sample at said controllable temperature and pressure;
    (b) means movable within said sample cell and means for moving said movable means to determinable positions within said sample cell;
    (c) means connected to said movable means for capturing a measured quantity of said sample and for maintaining said measured quantity at the temperature and pressure maintained within said sample cell;
    (d) means for moving said captured sample to means for measuring properties of said sample and for returning said captured sample to said sample cell without changing the temperature and pressure on said captured sample;
    (e) and means for making visual and/or electromagnetic energy observations from outside said sample cell on said sample contained within said sample cell.

2. The apparatus of claim 1 wherein said sample cell is a light transmitting material clamped in a metallic shell.

3. The apparatus of claim 1 wherein said sample holder is a sapphire tube.

4. The apparatus of claim 3 wherein said sapphire tube is a single crystal of 0° orientation.

5. The apparatus of claim 1 wherein said cell is constructed with at least one light transmitting window permitting observation of said sample within said sample cell.

6. The apparatus of claim 5 wherein said sample cell has at least one sapphire window as said light transmitting window and said sample cell is an outer steel shell encasing said window.

7. The apparatus of claim 1 wherein said cell is constructed with light transmitting windows formed from crystalline materials in the class including high strength glass, sapphire, diamond and transparent crystalline salts.

8. The apparatus of claim 1 wherein said means movable within said sample cell is a probe movable within said sample holder, said probe including means for moving said captured sample to said means for measuring.

9. The apparatus of claim 8 wherein said means for moving said captured sample is a mercury column moving in said probe means and within said sample cell without changing pressure in sample cell.

10. The apparatus of claim 8 wherein said probe includes means for flushing with fluids from within said sample cell to prevent contamination of captured samples.

11. The apparatus of claim 8 wherein said captured sample is a volume from 1 microliter to 300 microliters.

12. The apparatus of claim 1 wherein pressure within said sample cell is controlled by changing the volume within said sample cell with liquid mercury.

13. The apparatus of claim 1 wherein the temperature within said sample holder is maintained by surrounding said sample cell with a gaseous nitrogen bath and the nitrogen is heated or cooled to the desired temperature and circulated around said apparatus.

14. The apparatus of claim 1 wherein said entire apparatus is supported on a rotatable mounting to permit at least said sample cell to be inverted.

15. The apparatus of claim 1 including an explosion-proof housing.

16. The apparatus of claim 1 including a housing lined with a flexible plastic liner resistant to puncture.

17. The apparatus of claim 1 wherein said sample cell is capable of maintaining at least 20,000 pounds per square inch pressure on said sample.

18. The apparatus of claim 1 or 17 wherein said sample cell is capable of maintaining a range of temperatures between about −40° F. and about +400° F.

19. The apparatus of claim 18 including a gamma ray source and a gamma ray detector and wherein said measurement of density is accomplished by aligning said gamma ray source with respect to a phase of said sample within said sample cell and said gamma ray detector is aligned with respect to said gamma ray source and said sample cell to detect gamma rays transmitted through said sample within said sample cell.

20. Apparatus for measuring characteristics including composition, density, viscosity and interfacial tension of fluid phases of a petroleum based sample having vapor and/or liquid phases at the temperature and pressure existing where said sample was taken, said apparatus comprising:
  (a) a sample cell capable of maintaining said sample at a temperature and pressure at least as high as the temperature and pressure existing where said sample was taken, said sample cell having means for inserting a sample into said cell, means for controlling the pressure and temperature of said sample within said sample cell, and means for permitting visual and radiant energy observations from outside said sample cell on said sample contained within said sample cell;
  (b) a sample probe movable within said sample cell and means for moving said probe to determinable positions within said sample cell;
  (c) means for measuring composition of any phase within said sample cell by positioning said sample probe within said sample cell, and means for transporting a measurable quantity of said sample collected at said probe through said sample;
  (d) means for nondestructively measuring density of any phase within said sample cell by performing measurement techniques from outside of said sample cell on said phases of said sample within said sample cell at said temperature and pressure maintained within said sample cell;
  (e) means for nondestructively measuring viscosity on said sample contained within said sample cell;
  (f) and means for nondestructively measuring interfacial tension between phases of said sample within said sample cell at said pressure and temperature maintained with said sample cell.

21. The apparatus of claim 20 wherein said means for measuring viscosity includes a chamber containing a torsional piezoelectric quartz crystal and means for transporting a quantity of said sample from said sample cell to said chamber to surround said crystal with said sample whereby viscosity is measured by the resonant characteristics of said crystal enclosed in said sample at said temperature and pressure maintained within said sample cell.

22. The apparatus of claim 20 wherein said means for measuring viscosity includes means for transmitting a laser beam into said sample cell and means for detecting laser beam reflection from the vapor-liquid/liquid-liquid interface of said sample within said sample cell to a detecting means outside of said sample cell.

23. The apparatus of claim 20 wherein said means for measuring interfacial tension includes means for displacing at least one drop of one phase of said sample in the other phase of said sample from the tip of said sample probe, and means for measuring a characteristic of said drop within said sample cell at said temperature and pressure maintained within said sample cell through said means for permitting visual observation, said interfacial tension being determined by relating said measured characteristic to said measured densities of said phases of said sample.

24. The apparatus of claim 20 wherein said means for measuring interfacial tension includes means for transmitting a laser beam into said sample cell and means for detecting laser beam reflection from a surface of said sample within said sample cell to a detecting means outside said sample cell.

* * * * *